United States Patent [19]

Spillman, Jr.

[11] Patent Number: 5,440,300
[45] Date of Patent: Aug. 8, 1995

[54] SMART STRUCTURE WITH NON-CONTACT POWER AND DATA INTERFACE

[75] Inventor: William B. Spillman, Jr., Charlotte, Vt.

[73] Assignee: Simmonds Precision Products, Inc., Akron, Ohio

[21] Appl. No.: 345,205

[22] Filed: Nov. 28, 1994

Related U.S. Application Data

[63] Continuation of Ser. No. 981,966, Nov. 25, 1992, abandoned.

[51] Int. Cl.⁶ .................................................. G08C 17/00
[52] U.S. Cl. ........................... 340/825.54; 250/227.21; 73/146.5; 73/724; 340/448
[58] Field of Search .................... 250/227.14; 73/146.4, 73/146.5, 598, 599, 601, 781, 782; 340/445, 446, 447, 448, 449, 668, 683, 825.54, 870.15, 870.16, 870.31; 623/3; 606/15, 16; 128/660.02, 666, 667, 670, 672, 673, 674, 675, 697, 903

[56] References Cited

U.S. PATENT DOCUMENTS

| | | | |
|---|---|---|---|
| 2,447,734 | 8/1948 | Capuzzi | 323/75 |
| 3,224,257 | 12/1965 | Takami et al. | 73/88.5 |
| 3,310,736 | 3/1967 | Bayly et al. | 324/62 |
| 3,588,687 | 6/1971 | Kohler . | |
| 3,719,935 | 3/1973 | Chaney et al. | 340/206 |
| 3,758,845 | 9/1973 | MacKelvie et al. | 323/51 |
| 3,876,998 | 4/1975 | Richter et al. | 340/189 |
| 4,002,967 | 1/1977 | Fennell | 324/40 |
| 4,223,300 | 9/1980 | Wiklund | 340/196 |
| 4,225,851 | 9/1980 | Reschovsky et al. | 340/177 CA |
| 4,367,460 | 1/1983 | Hodara . | |
| 4,425,511 | 1/1984 | Brash . | |
| 4,470,300 | 9/1984 | Kobayashi | 73/304 C |
| 4,567,459 | 1/1986 | Folger et al. | 340/58 |
| 4,578,992 | 4/1986 | Galasko et al. . | |
| 4,590,466 | 5/1986 | Wiklund . | |
| 4,646,066 | 2/1987 | Baughman et al. | 340/540 |
| 4,682,104 | 7/1987 | Lombard et al. . | |
| 4,717,905 | 1/1988 | Morrison et al. . | |
| 4,725,839 | 2/1988 | Crowe . | |
| 4,741,341 | 5/1988 | Marach | 128/697 X |
| 4,743,786 | 5/1988 | Ichikawa et al. | 310/111 |
| 4,781,056 | 11/1988 | Noel et al. . | |
| 4,800,755 | 1/1989 | Fathauer et al. | 73/304 |
| 4,808,911 | 2/1989 | Oaks | 324/57 Q |
| 4,891,973 | 1/1990 | Bollweber et al. | 73/146.5 |
| 4,900,921 | 2/1990 | Spillman, Jr. | 250/577 X |
| 4,904,863 | 2/1990 | McDearmon . | |

(List continued on next page.)

FOREIGN PATENT DOCUMENTS

| | | |
|---|---|---|
| 3412610A1 | 10/1985 | Germany . |
| 3810702A1 | 10/1989 | Germany . |
| 4006007A1 | 8/1990 | Germany . |
| 3922556A1 | 1/1991 | Germany . |
| 4023412A1 | 2/1992 | Germany . |
| 4033052A1 | 4/1992 | Germany . |
| 4034019C1 | 7/1992 | Germany . |
| 62-049279 | 3/1987 | Japan . |
| 3274420 | 12/1991 | Japan . |
| 4116425 | 4/1992 | Japan . |
| WO9100985 | 7/1990 | WIPO . |
| WO9100985 | 1/1991 | WIPO . |

OTHER PUBLICATIONS

Masri et al., "Structure-unknown non-linear dynamic systems: identification through neural networks," pp. 45-56, copyright 1992 IOP Publishing Ltd.

*Primary Examiner*—Tod R. Swann
*Attorney, Agent, or Firm*—Leonard L. Lewis; William E. Zitelli

[57] ABSTRACT

Embedded smart structures include active electronics which control and collect data from sensors and actuators and transmit data to the exterior of a body by electromagnetic antenna radiation to a conformal power and data interrogation interface. Multiple embedded smart structures are powered and interrogated by a network of conformal powering and interrogation units. Multiple embedded sensors each having an antenna with a defined narrow band resonant frequency are powered and interrogated by a single external powering and data interrogation antenna.

19 Claims, 3 Drawing Sheets

U.S. PATENT DOCUMENTS

| | | | |
|---|---|---|---|
| 4,922,096 | 5/1990 | Brennan | 250/227.14 |
| 4,930,852 | 6/1990 | Wheeler et al. | 250/227.14 |
| 4,983,034 | 1/1991 | Spillman, Jr. | 250/227.14 |
| 4,984,863 | 1/1991 | Parriaux et al. | |
| 5,005,409 | 4/1991 | Hochstein | 73/304 |
| 5,049,856 | 9/1991 | Crossfield | |
| 5,058,436 | 10/1991 | Bellec et al. | 73/727 |
| 5,086,274 | 2/1992 | Gobin et al. | |
| 5,107,833 | 4/1992 | Barsness | 128/903 X |
| 5,140,696 | 8/1992 | Fox | 455/41 |
| 5,144,299 | 9/1992 | Smith | |
| 5,150,115 | 9/1992 | deJong et al. | 340/870.31 |
| 5,153,583 | 10/1992 | Murdoch | 340/825.54 |
| 5,165,283 | 11/1992 | Kurtz et al. | 73/727 |
| 5,181,423 | 1/1993 | Phillipps et al. | 340/870.31 |
| 5,196,845 | 3/1993 | Myatt | 340/870.31 |
| 5,278,442 | 1/1994 | Prinz et al. | 257/417 |

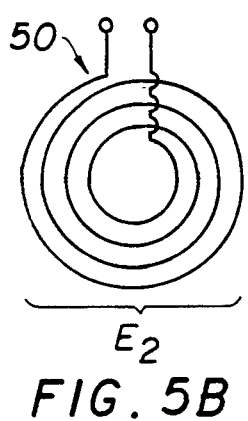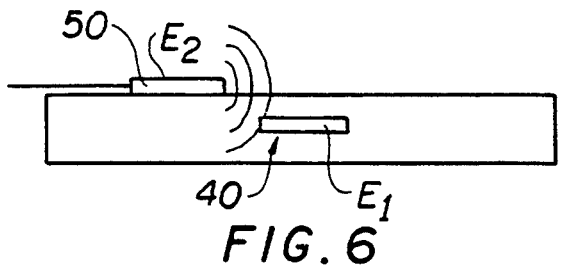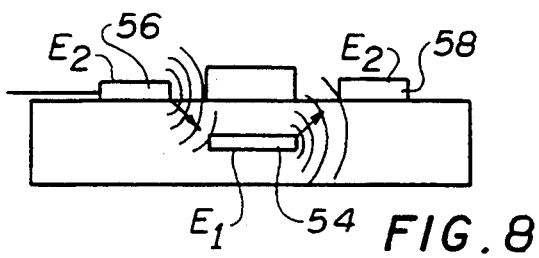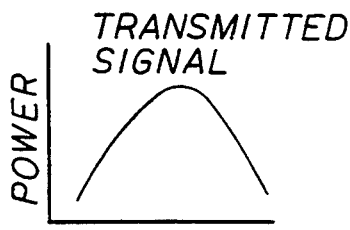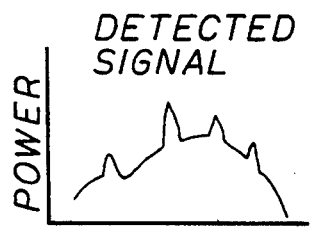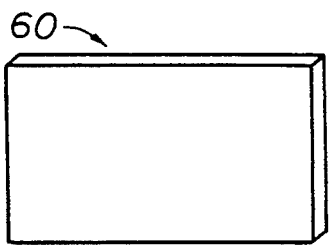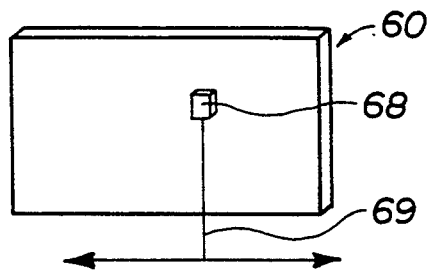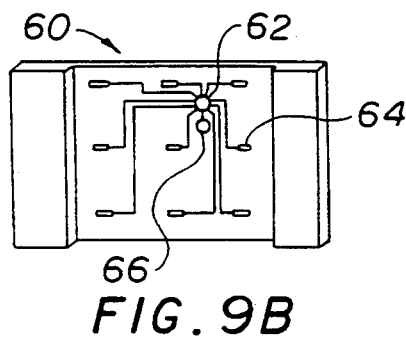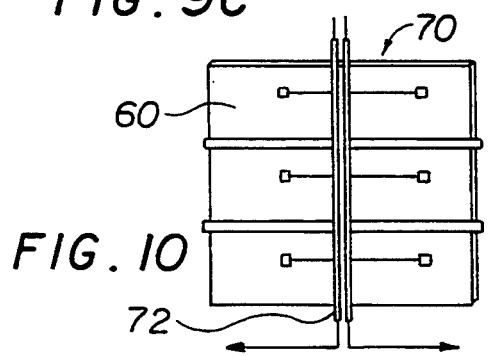

SMART STRUCTURE WITH NON-CONTACT POWER AND DATA INTERFACE

This is a continuation of application Ser. No. 07/981,966, filed on Nov. 25, 1992, now abandoned.

BACKGROUND OF THE INVENTION

The present invention relates to smart structures, and in particular smart structures having embedded sensors and actuators.

Devices such as capacitive sensors and switches have been embedded within bodies to perform as remote sensing devices. It is further known that limited types of information can be accessed from such sensors without the need for direct physical connection to the exterior of the body in which they are embedded. For example a passive antenna circuit has been installed within a tire and utilized from the exterior of the tire to determine changes in tire pressure which affect the antenna circuit resonance. It also has been suggested that an artificial heart can be electrically powered from the exterior of the body by antenna radiation of electromagnetic energy. Such devices, however, are unsuitable for complex structures. For example, in the context of an aircraft structure, there is a need for multiple and varied active sensing and actuating functions to be performed at many locations throughout the aircraft without direct power and data connections to each location.

SUMMARY OF THE INVENTION

The present invention provides methods and apparatus for sensing, processing, and receiving data from embedded structures without direct physical connection between the embedded structures and a data collection and powering interface. In a preferred embodiment, the invention contemplates a smart structure having sensing means embedded in a body, electromagnetic means for transmitting power to the sensing means, means exterior to the body for receiving data from the sensing means, wherein the sensing means comprises data control means connected to electromagnetic means for transmitting data to said exterior receiving means.

These and other aspects of the present invention will be readily understood and appreciated by those skilled in the art from the following detailed description of the preferred embodiments with the best mode contemplated for practicing the invention, in view of the accompanying drawings.

BRIEF DESCRIPTION OF THE DRAWINGS

FIGS. 5A and 5B illustrate different embodiments for powering and receiving antennae in accordance with the present invention;

FIG. 6 illustrates electromagnetic coupling of two antennae in accordance with the present invention;

FIG. 7A and 7B illustrate representative power and frequency distributions of transmitted and detected signals of antennae in accordance with the present invention;

FIG. 8 illustrates electromagnetic coupling of antennae in accordance with the present invention;

FIGS. 9A, 9B and 9C illustrate a smart structure panel in accordance with the present invention;

FIG. 10 illustrates an assemblage of smart structure panels in accordance with the present invention.

DETAILED DESCRIPTION OF PREFERRED EMBODIMENTS

Figure 1:
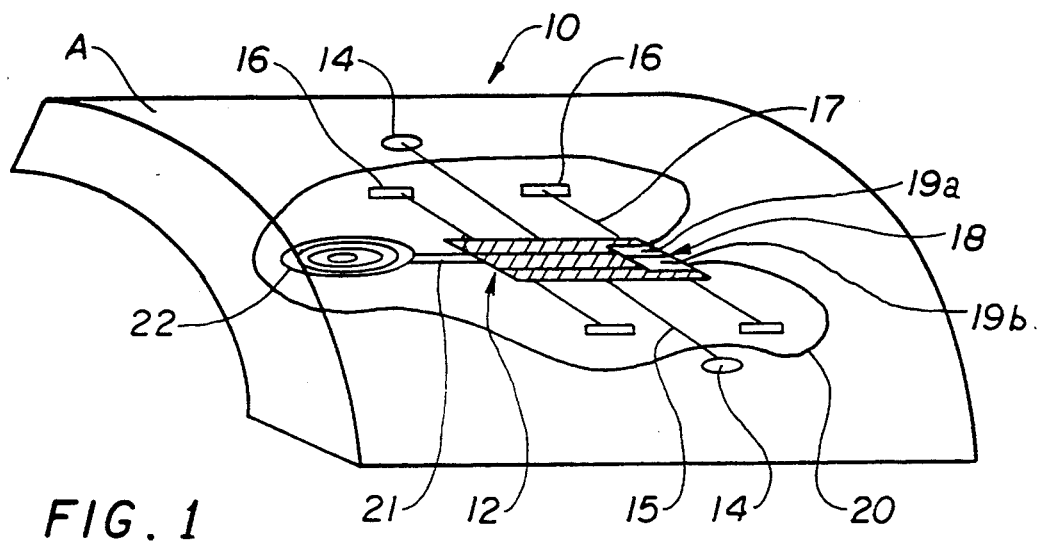
FIG. 1 illustrates an embedded smart structure in accordance with the present invention.

FIG. 1 illustrates one embodiment of an embedded smart structure, indicated generally at 10. As illustrated, the structure includes a body A which may be of any shape or configuration and made of any materials such as carbon fiber composite materials. Embedded structure 10 includes data control devices such as active data collection and processing electronics, indicated generally at 12, in which electrical sensors 14 may be incorporated and/or extend from by connections 15 as shown. Data collection and processing electronics 12 may include circuitry for performing analog to digital conversion, AC to DC conversion, frequency to voltage conversion, semiconductor light sources and optical wavelength detectors which convert light to electrical signals, modulators, power storage, and microprocessing devices. This list is not exhaustive but rather exemplary of the types of sensors, actuators and control devices that may be embedded in the structure 10.

For example, sensors 14 can be of any type suitable for detection of stress, strain, vibration, cracks or separation, chemical changes or temperature or any other physical data obtainable from within body A. Embedment of sensors 14 as part of the smart structure enables selective placement of each sensor within body A based upon the condition to be monitored.

Data collection and processing electronics 12 may also include optical sensing and detection means, such as a modal domain vibration sensor, indicated generally at 18. A light source 19a, such as a laser diode light source, is connected to at least one multimode optical fiber 20 which extends from optical source 19a about the area in which the electronics 12 are embedded. Optical fiber 20 is return connected to a small area optical detector 19b which detects changes in light intensity as a result of perturbation or vibration of the fiber, and converts the changes to electrical signals which are fed to electronics 12.

Actuators 16, connected to the data collection and processing electronics 12 by connections 17, are electrically activated by electronics 12 to perform physical functions within body A. For example, actuators 16 may be piezoelectric devices which perform expansion or contraction of body A in proximity to the embedded actuator or shape memory alloy actuators.

Also connected to data collection and processing electronics 12 by electrical connection 21 is an electromagnetic antenna 22. Antenna 22 is illustrated in a looped circular or concentric configuration but may be of any suitable shape or orientation for any particular application. Antenna 22 provides transmission of data collected and processed by electronics 12 and further functions to receive electromagnetic energy from a coupled external electromagnetic antenna as described below to transmit power to electronics 12 at a reserved frequency. Each of the sensors 14 and actuators 16 are powered by data collection and processing electronics 12 by electromagnetic power received through antenna 22. The data of each of the sensors 14 is combined into a common electrical signal by processing electronics 12 which can be amplitude or frequency modulated to differentiate the input of each of the different sensors. The collected and modulated data of sensors 14 is then transmitted by antenna 22 to an external receiving antenna preferably at a frequency different from the reserved powering frequency.

Figure 2:
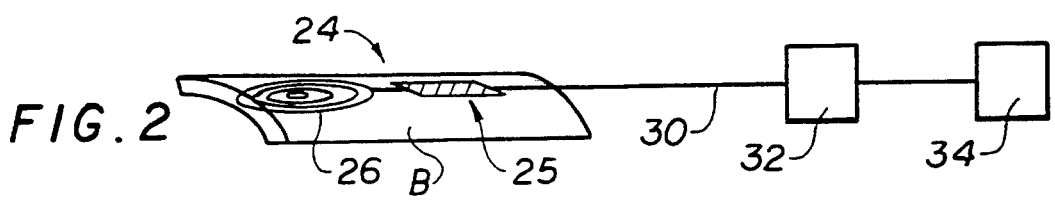
FIG. 2 illustrates a conformal powering and interrogative electromagnetic interface in accordance with the present invention.

FIG. 2 illustrates a conformal powering and data reception interrogation interface unit, indicated generally at 24, which includes electronics 25 and powering/reception antenna 26 embedded in body B. The term "conformal" as used herein refers to the physical configuration of body B which is formed to physically match the exterior contour of the surface area of body A below which structure 10 is embedded. Powering and data interface antenna 26, connected to electronics 25, may be looped or concentric or of any other configuration suitable for electromagnetic coupling with antenna 22. Antenna 26 is connected to powering and data collection electronics 25, also embedded within conformal piece 24, and connected to a data and power bus cable 30 which leads to a power source 32 and information processing and display means 34. Powering and data collection electronics 25 provides power to the antenna 26 which emits electromagnetic energy in an appropriate frequency band to the embedded antenna 22 for supplying power to the smart structure 10. The antenna 24 also receives electromagnetic energy from the antenna 22 which is encoded with the sensor data from the embedded electronics 12 and processed the received signal for transmission along data bus 30. The interrogation interface piece 24 can be fixed in position relative to an embedded structure or used as a mobile interrogator for periodic area analysis and/or activation. The antenna 24 and associated electronics 25 can also be used, of course, for transmitting data to the smart structure 10.

By electromagnetic coupling of powering and reception antenna 26 and data collection and processing antenna 22, the embedded structure 10 is powered and interrogated by a single conformal interface without hardwire connections. The coupling of antennas as for example between antenna 22 shown in FIG. 1 and antenna 26 shown in FIG. 2, can be of any suitable configuration in which predetermined frequency bands can be matched within an optimum electromagnetic transmission window of the material in which the structures are embedded. Preferably each sensor will have a corresponding predetermined frequency band. Sensors 14 and/or 18 and/or actuator 16 are activated by data collection and processing electronics 12 which collects the data of the various sensors and can determine the status of actuators and in return transmit information along the same path.

Figure 3:
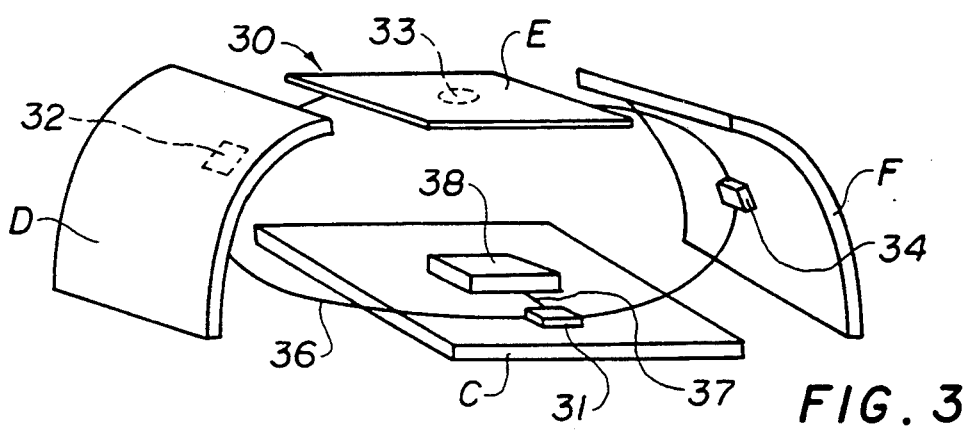
FIG. 3 illustrates a network of embedded smart structures in accordance with the present invention.

FIG. 3 illustrates an embodiment of a multiple embedded structure network 30 wherein several smart structures embedded within panels C, D, E and F are powered and interrogated by a network of conformal powering and data reception interrogation interface units 31 through 34 which are connected by and serve as nodes along a common power/data bus cable 36. Each of the panels C through F may be smart structures such as structure 10 of FIG. 1 including sensors and/or actuators, data collection and processing electronics, and a data collection and transmitting antenna. The power/data bus cable 36 is connected by line 37 (through interface unit 31) to a central processing control unit 38 which collects data from each of the interface units of the network 30 which comprises data from each of the smart structures embedded in panels C through F. The power/data bus cable 36 may be electrical and/or include fiber optic cable for data communication. In this manner, a multiplicity of embedded smart structures can be powered, controlled and interrogated by a central processing and control unit.

Figure 4:
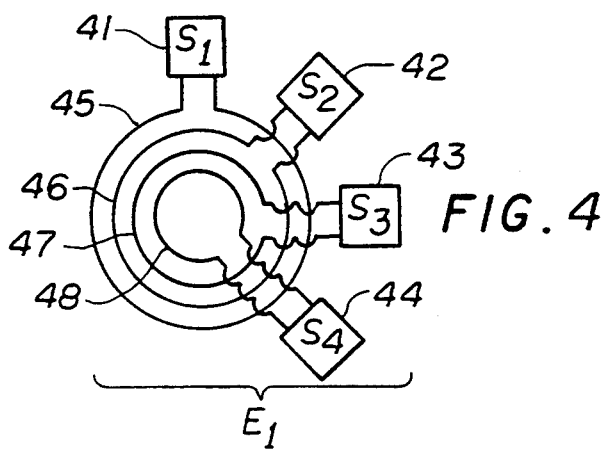
FIG. 4 illustrates an array of multiple embedded devices in accordance with the present invention.

With reference to FIG. 4, a single power and interrogation antenna can be coupled with multiple sensor antennae in a multiplexing arrangement. Sensors 41 through 44, each with incorporated active electronics such as described with reference to FIG. 1, or alternatively with passive electronics, each have a dedicated corresponding antenna 45 through 48 which may be arranged concentrically as shown. In this embodiment, each concentric antenna 45 through 48 has its own distinct and predetermined transmission band resonant frequency. The sensor electronics of sensors 41 through 44, are configured so that changes in the detected parameter of interest induce resonant frequency band shifts within the predetermined frequency band transmitted by the corresponding antenna.

Figure 5A:
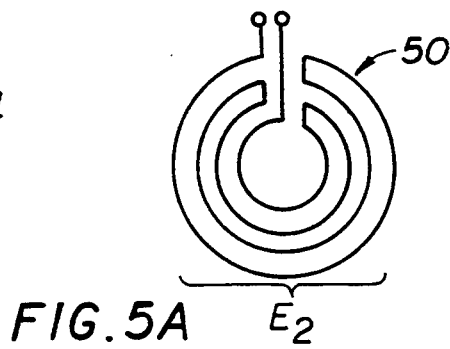

The concentric antenna array of multiple sensors can be positioned for electromagnetic coupling to a single power/interrogation antenna 50 such as illustrated by FIGS. 5A and 5B which may be, but is not limited to one of the coiled configurations shown. When excited by the appropriate drive current, the power/interrogation antenna 50 generates a broad band RF single that contains components at all of the narrow band resonant frequencies of sensor antennas 45 through 48 for powering the sensors and receiving the data transmission from each sensor.

As illustrated in FIG. 6, the doughnut shaped radiation pattern of a concentric or looped antenna such as power/interrogation antenna 50 fixed to a surface of a body electromagnetically interfaces with an embedded sensor array 40. As energy is radiated from power/interrogation antenna 50, the narrow band resonances of sensor antennae 45 through 48 are excited providing power to the corresponding sensors 41 through 44. The collected data of which is reradiated for detection by antenna 50. Representative plots of the signal transmitted from antenna 50 and the return signal detected by antenna 50 are illustrated in FIG. 7A and 7B, respectively.

In a similar manner, an embedded sensor or sensor array 40 can be interrogated by, and serve as a transmission element between two power/interrogation antennae. As illustrated in FIG. 8, an embedded sensor and accompanying antenna 54 is positioned between two power/interrogation antennae 56 and 58. In this embodiment, embedded sensor 54 receives a power signal from antenna 56 and transmits a detected data signal to antenna 58. This embodiment is particularly useful in applications where direct linear coupling of a power/interrogation antenna with an embedded structure, or where direct coupling of two surface mounted transmission antennae is not possible. Of course, the embedded sensor 54 may consist of an array of sensors, such as described with reference to FIG. 4. Thus, it is shown that non-contact multiplexing of a number of sensors can be carried out without the need for an electrical power source at the sensing location.

FIGS. 9A through 9C illustrate one embodiment of a modular construction of a "smart panel" 60. The smart panel 60 may be made of any material which is compatible with, and suitable for, implanting of electronics such as composites. As shown in FIG. 9B, the panel 60 contains in its interior volume a thin film electronics package 62 with sensors 64 and RF antenna 66 extending therefrom. As shown in FIG. 9C, the self-contained and sealed panel 60 is then powered and interrogated by an non-contact RF coupling 68 connected to data/power bus cable 69. The use of thin film flexible electronics within the panel 60 enables the panel 60 to be of flexed or curved configuration. As shown in FIG. 10, multiple panels can be arranged in adjacent fashion to form a smart structure system 70 illustrated in FIG. 10, with a common power/data bus cable 72.

Figure 11:
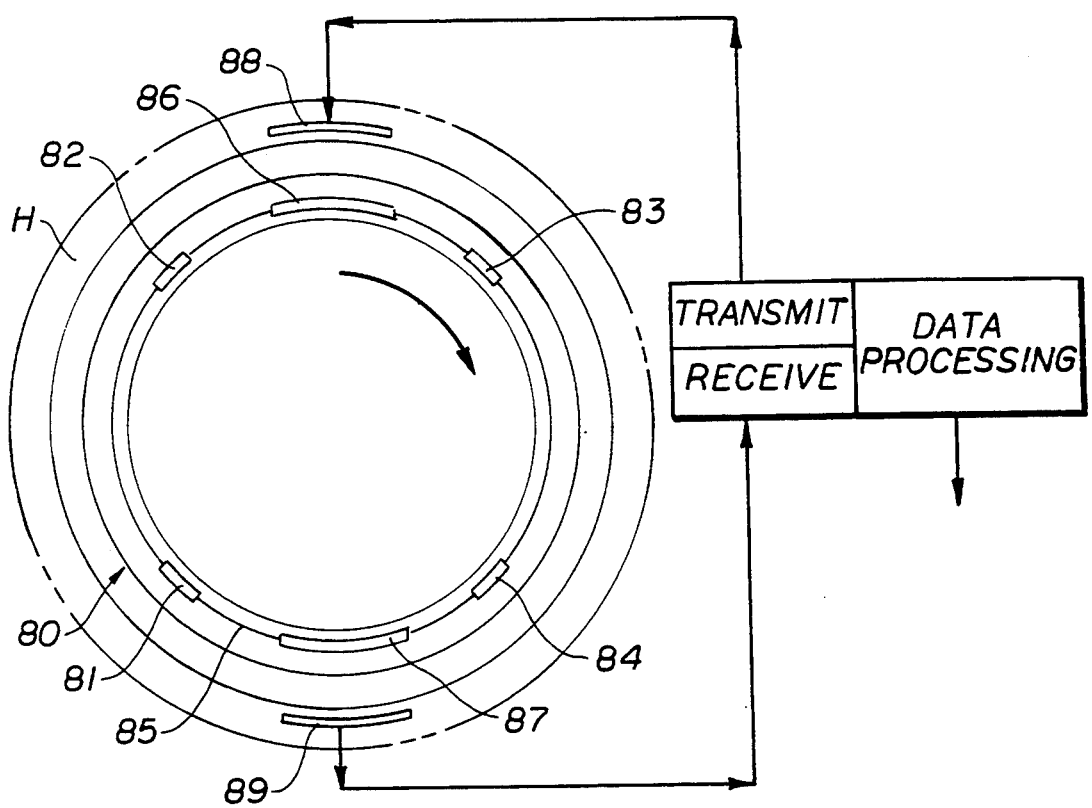
FIG. 11 illustrates a cross-section of a shaft in which sensors are embedded and a shaft housing in accordance with the present invention.

FIG. 11 illustrates an embodiment and use of embedded electronic structures within a rotating shaft 80. Embedded below the surface of the shaft are sensors 81 through 84 which can be connected via a common power/data bus cable 85 as described with reference to FIG. 3. Sensors 81 through 84 may be, for example, piezo-ceramic vibration sensors, strain gauges and may also include accompanying electronics similar to structure 10 of FIG. 1 including charge storage capacity. Cable 85 also intersects with embedded antennae 86 and 87 which though shown in profile can be of a looped or concentric configuration such as antennae 22 described with reference to FIG. 1. A transmitting antenna 88 physically matched for optimum electromagnetic coupling with antennae 86 and 87 is positioned within shaft housing H to transmit power to antennas 86 and 87 as they rotate past antenna 88. Similarly, a reception antenna 89 is positioned within shaft housing H diametrically opposite transmission antenna 88 to receive data collected by antennae 86 and 87 from sensors 81 through 84 as the rotational position of reception antenna 89 is passed. As power reception antenna 86 aligns with powering antenna 88, each of the sensors 81 through 84 is powered and send respective signals to data transmitting antenna 87 for electromagnetic transmission to receiving antenna 89. Such transmission across the diameter of the shaft can be used to obtain a reading on the rate of rotation of the shaft. This can be accomplished by, for example, embedding a dummy sensor in the shaft 80 to provide a reference signal relative to the diametrically opposed antennae. Thus, operational and physical data such as vibration, temperature, rate of rotation, expansion, moisture can be collected from shaft body 80 without direct physical connection to the shaft or any shaft bearing mechanism.

While the invention has been shown and described with respect to specific embodiments thereof using detailed schematics and words, this is for the purpose of illustration rather than limitation, and other variations and modifications of the specific embodiments herein shown and described will be apparent to those skilled in the art within the intended spirit and scope of the invention as set forth in the appended claims.

What is claimed is:

1. A smart structure, comprising:
structural material forming a body,
sensing means including at least one sensor embedded in the material of the body, wherein the sensor detects a physical condition of the body,
a first antenna means embedded in the material of the body and connected to said embedded sensing means,
a second antenna means exterior the body for transmitting power to said sensing means; and
means exterior to the body for receiving data transmitted from said sensing means; wherein said embedded sensing means comprises data control means connected to said sensor and said first antenna means for transmitting said data to said exterior receiving means.

2. The structure of claim 1, including a second body; wherein said means for receiving data and said second antenna means for transmitting power are embedded in the second body that is conformal to a surface of the first stated body: said second body being disposed adjacent said first body such that said first and second antenna means are inductively coupled.

3. The structure of claim 1, wherein said sensing means comprises multiple embedded sensors connected to said data control means.

4. The structure of claim 1, wherein said embedded sensing means includes data collection, processing and conditioning electronics.

5. The structure of claim 4, wherein said embedded sensing means includes at least one sensing element connected to said data collection processing and conditioning electronics.

6. The structure of claim 5, wherein said embedded sensing means includes at least one actuator connected to said data collection processing and conditioning electronics.

7. The structure of claim 4, wherein said embedded sensing means includes an optical source and an optical sensor connected to said optical source.

8. The structure of claim 7, wherein said optical sensor includes an optic fiber.

9. The structure of claim 1, wherein said first antenna means is in a looped concentric configuration.

10. The structure of claim 9 further comprising multiple embedded sensing means receiving power via said first antenna means and further wherein each said sensing means produces data that is transmitted to said receiving means within a predetermined frequency band.

11. The structure of claim 2, wherein said exterior means for receiving data comprises said second antenna means that is also used for transmitting power to said sensing means; and further wherein said receiving means and second antenna means are embedded in said second body which is fixedly attached to the first body in which said sensing means is embedded.

12. The smart structure of claim 1 wherein said body comprises composite materials with each sensor embedded therein.

13. The smart structure of claim 12 wherein said body is a structural member of an aircraft.

14. An embedded smart structure system comprising:
structural material forming a body,
at least two sensors embedded in the material of the body wherein each sensor operates on a physical condition of the body,
said sensors being connected to an antenna means embedded in the material of the body and which receives a power signal for powering said sensors and which transmits data signals from each said sensor in a respective predetermined frequency band, and
an antenna exterior to said body and positioned for electromagnetic coupling with said embedded antenna connected to said sensors, wherein said exterior antenna emits a broad frequency band power signal and receives transmitted data signals from said embedded antenna.

15. The system of claim 14 comprising multiple embedded sensors and respective antennae wherein said embedded antennae are concentrically arranged.

16. The system of claim 15 wherein said exterior antenna is of a configuration which physically overlaps said embedded antennae and transmits power to all said embedded sensors.

17. The system of claim 14 comprising multiple sensors each operating with respective predetermined frequency bands for data transmission, said exterior antenna emitting a broad band power signal that includes all of said predetermined frequency bands.

18. The system of claim 14 comprising a plurality of composite matrix bodies, each body having embedded sensors and a respective antenna means embedded therein; and a corresponding plurality of exterior antennas, each exterior antenna being in fixed spatial position with respect to its corresponding embedded antenna means; all said exterior antennas being connected to a control means for powering said sensors and receiving data therefrom.

19. The system of claim 18 wherein each embedded antenna means comprises a plurality of antennas in a looped and generally concentric configuration, with each looped antenna being connected to respective embedded sensors so as to transmit data to its corresponding exterior antenna for each sensor connected thereto at a predetermined frequency band.

* * * * *